United States Patent
Tanaka et al.

(10) Patent No.: US 7,270,698 B2
(45) Date of Patent: Sep. 18, 2007

(54) DISCHARGE DEVICE AND AIR PURIFIER

(75) Inventors: Toshio Tanaka, Osaka (JP); Kenkichi Kagawa, Osaka (JP); Kanji Motegi, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 245 days.

(21) Appl. No.: 10/525,868

(22) PCT Filed: Jun. 7, 2004

(86) PCT No.: PCT/JP2004/008249

§ 371 (c)(1),
(2), (4) Date: Feb. 25, 2005

(87) PCT Pub. No.: WO2004/108294

PCT Pub. Date: Dec. 16, 2004

(65) Prior Publication Data

US 2005/0257687 A1    Nov. 24, 2005

(30) Foreign Application Priority Data

Jun. 5, 2003    (JP)    ............................. 2003-161258

(51) Int. Cl.
*B03C 3/40*    (2006.01)
(52) U.S. Cl. .................... 96/95; 96/97; 96/98
(58) Field of Classification Search ............. 96/95–100
See application file for complete search history.

(56) References Cited

U.S. PATENT DOCUMENTS

| | | | | |
|---|---|---|---|---|
| 3,765,154 A | * | 10/1973 | Hardt et al. ................... 96/88 |
| 4,375,364 A | * | 3/1983 | Van Hoesen et al. ........... 96/87 |
| 4,675,029 A | * | 6/1987 | Norman et al. ................. 95/73 |
| 4,948,399 A | * | 8/1990 | Reuffurth et al. .............. 96/92 |
| 5,322,550 A | * | 6/1994 | Park .............................. 96/66 |
| 5,695,549 A | * | 12/1997 | Feldman et al. ............... 96/55 |
| 6,042,637 A | * | 3/2000 | Weinberg ........................ 96/58 |
| 6,077,334 A | * | 6/2000 | Joannou ........................ 96/66 |
| 6,092,387 A | * | 7/2000 | Hironaka et al. ............. 62/317 |
| 6,287,368 B1 | * | 9/2001 | Ilmasti .......................... 96/19 |
| 6,375,714 B1 | * | 4/2002 | Rump et al. ..................... 95/3 |
| 2002/0008480 A1 | | 1/2002 | Yamazaki et al. ....... 315/111.21 |
| 2006/0032376 A1 | * | 2/2006 | Osada et al. ................. 96/96 |

FOREIGN PATENT DOCUMENTS

| | | |
|---|---|---|
| JP | 10-296126 A | 11/1998 |
| JP | 11-067423 A | 3/1999 |
| JP | 2001-218828 A | 8/2001 |
| JP | 2001-239239 A | 9/2001 |
| JP | 2002-93768 A | 3/2002 |
| JP | 2002-159829 A | 6/2002 |
| JP | 2002-336689 A | 11/2002 |
| JP | 2002-345938 A | 12/2002 |
| JP | 2002-361028 A | 12/2002 |
| JP | 2003-053129 A | 2/2003 |
| JP | 2003-109794 A | 4/2003 |

* cited by examiner

*Primary Examiner*—Richard L. Chiesa
(74) *Attorney, Agent, or Firm*—Global IP Counselors (57) ABSTRACT

The distance between a discharge electrode and a counter electrode of a discharge device is set to not more than 10 mm such that a streamer discharge is caused between the electrodes. The frequency of sound made by the streamer discharge is raised to 6 kHz or higher to exceed the frequency range which is easily perceivable by human hearing.

4 Claims, 8 Drawing Sheets

DISTANCE (L) BETWEEN ELECTRODES (13) AND (14) (mm)

DISCHARGE DEVICE AND AIR PURIFIER

BACKGROUND OF THE INVENTION (a) Field of the Invention

The present invention relates to a discharge device which performs streamer discharge and an air purifier. In particular, it relates to a technology for reducing noise of streamer discharge.

(b) Background Information

Air purifiers provided with discharge devices have conventionally been used as a means of decomposing and removing odorous components and hazardous components by using plasma generated by discharge. Among various discharge-based air purifiers, a streamer discharge-based air purifier is suitable for decomposition of the hazardous components and deodorization due to its high decomposition efficiency at a relatively low electric power.

Figure 8:
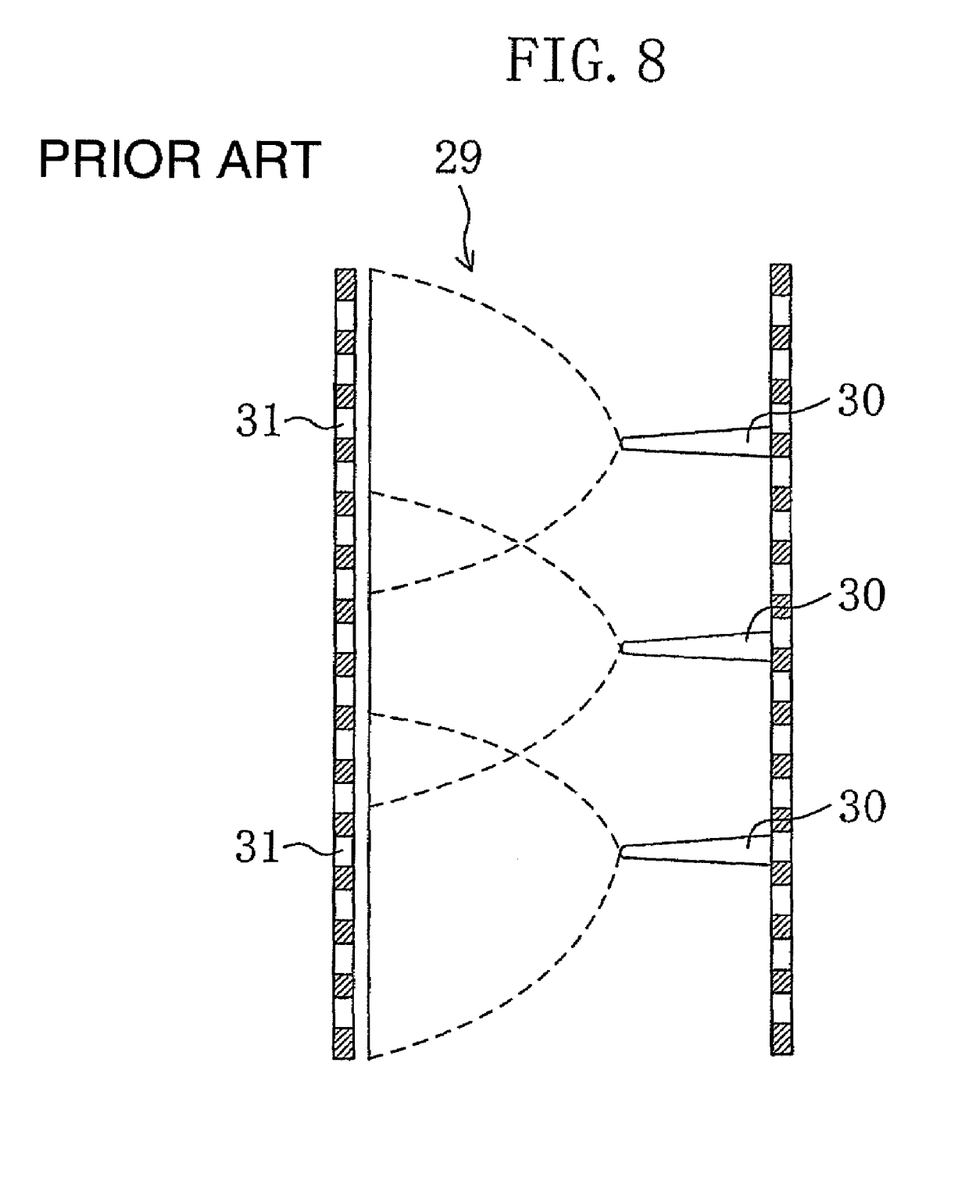
FIG. 8 is a schematic view illustrating a conventional discharge device.

FIG. 8 shows a schematic configuration of a discharge device in an air purifier. The discharge device (29) includes projecting discharge electrodes (30) for generating low temperature plasma and flat counter electrodes (31) opposed to the tips of the discharge electrodes (30). Discharge is caused between the electrodes (30) and (31) to generate the low temperature plasma, and then a target gas is introduced therebetween to allow hazardous components and odorous components contained in the target gas to contact active species (fast electrons, ions, radicals and other excited molecules) generated by the low temperature plasma. In this way, these components are decomposed and removed (for example, see Japanese Unexamined Patent Publication No. 2002-336689).

However, streamer discharge makes a relatively loud discharge sound due to electrical breakdown in the air. Since the frequency range of the discharge sound is significantly likely to be perceived by human hearing, the discharge sound caused by the operation of a streamer discharge-based air purifier may possibly be recognized as a noise. Therefore, the streamer discharge-based air purifier is regarded as unsuitable for places where certain silence is required such as living space and small stores. However, to put it the other way around, if the discharge sound made by streamer discharge can be reduced, streamer discharge will be applicable to compact air purifiers for consumer use. That is, it will be possible to make full use of the high decomposition efficiency of streamer discharge in a wide range of fields.

SUMMARY OF THE INVENTION

Under the above-described circumstances, the present invention has been achieved. An object of the present invention is to reduce noise of a discharge device which performs streamer discharge to make the discharge device applicable to consumer air purifiers, thereby improving the performance of the air purifiers.

The present invention is directed to reduce noise during streamer discharge by increasing the frequency of sound made by streamer discharge to a level higher than the frequency range which is easily perceivable by human hearing.

More specifically, a first invention of the present application relates to a discharge device comprising: a discharge electrode (13); a counter electrode (14) which is opposed to the discharge electrode (13); and a power source (18) connected to both of the discharge electrode (13) and the counter electrode (14) to apply a discharge voltage thereto, the discharge electrode (13) and the counter electrode (14) causing streamer discharge therebetween.

A feature of the discharge device is that the discharge electrode (13) and the counter electrode (14) are so configured that the frequency of sound made by streamer discharge is controlled to 6 kHz or higher.

The "frequency of sound" described herein is the center frequency of the discharge sound caused by electric current flowing in the pulse form during streamer discharge. Since the discharge sound actually made by discharge shows variations in frequency, its center frequency is the frequency at which the highest sound pressure level of the discharge sound is obtained in the measurement on a frequency-by-frequency basis.

Now, a detailed explanation is given of a relationship between the sensitivity of the human hearing and the frequency of sound.

The sensitivity of the human hearing to sound varies depending on the frequency of the sound. Therefore, for determining the magnitude of sound using a sound level meter or the like, in general, suitable numeric correction is carried out for each frequency of the sound so that the determined magnitude approaches the magnitude perceivable by the human hearing. For example, as specified in a sound measurement method conforming to JIS C 1502 "sound level meters", a correction factor referred to as A characteristic is added to or subtracted from the sound pressure level depending on the frequency thereof. Thus, every sound level approaches nearest the audible sensitivity of the human hearing.

When the frequency is in the range of about 1 kHz or higher to less than 6 kHz, the correction factor is a positive value. This indicates that the human hearing recognizes the sound in this range as relatively strong sound. On the other hand, when the frequency is 6 kHz or higher, the correction factor is a negative value, indicating that the human hearing recognizes the sound in this range as relatively weak sound. Thus, the frequency of the sound generated has a great influence on the sound level perceived by human hearing. If the center frequency of the sound generated can be raised to 6 kHz or higher, the sound level which is actually perceived by the human hearing will be reduced with efficiency.

In the first invention, the electrodes (13) and (14) are so configured that the frequency (center frequency) of the sound made by streamer discharge is controlled to 6 kHz or higher. Accordingly, the frequency of the discharge sound exceeds the range of 1 kHz or higher to less than 6 kHz which is easily perceivable by the human hearing. Therefore, the noise during streamer discharge is reduced.

According to a second invention, a discharge device comprises: a discharge electrode (13); a counter electrode (14) which is opposed to the discharge electrode (13); and a power source (18) connected to both of the discharge electrode (13) and the counter electrode (14) to apply a discharge voltage thereto, the discharge electrode (13) and the counter electrode (14) causing streamer discharge therebetween.

A feature of the discharge device is that the discharge electrode (13) and the counter electrode (14) are so configured that the residence time of charged particles (22) generated by streamer discharge is controlled to 0.17 ms or less.

Here, an explanation is given of the mechanism of streamer discharge and the residence time of charged particles (22).

Figure 4:
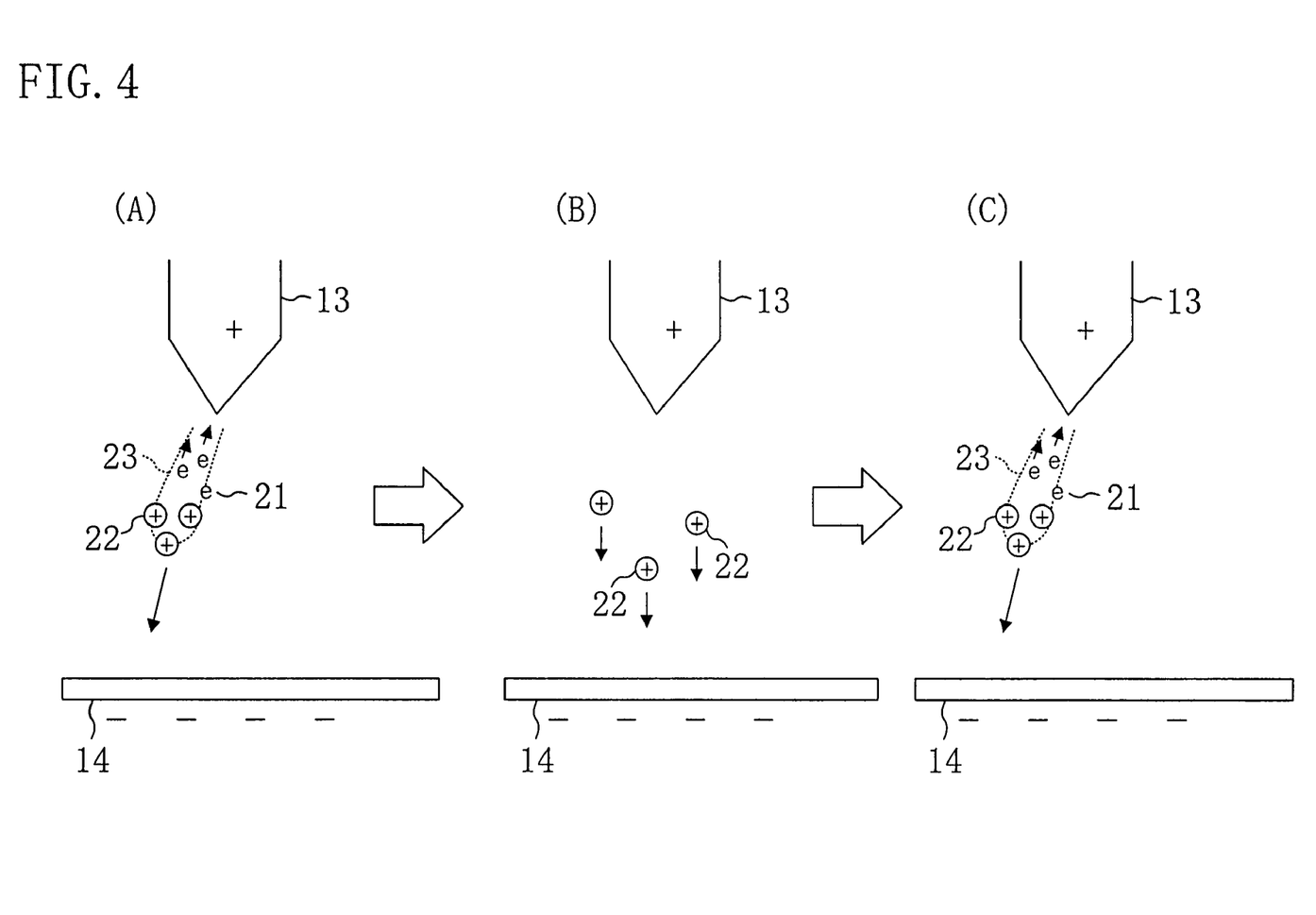
FIGS. 4A, 4B and 4C are views illustrating the mechanism of streamer discharge.

FIGS. 4A, 4B and 4C are step-by-step views illustrating the movement of the electrons (21) and the charged particles (22) (positive ions) during streamer discharge.

During streamer discharge, minuscule arc referred to as a leader (23) is generated from the discharge electrode (13) toward the counter electrode (14). At the tip of the leader (23), air is ionized into the electrons (21) and the charged particles (22) by a high potential gradient. A single discharge step is completed when the charged particles (22) reach the counter electrode (14).

The electrons (21) generated by the ionization move to the discharge electrode (13), while the charged particles (22) move to the counter electrode (14) (see FIG. 4A). Since the charged particles (22) generated by the ionization are relatively larger in mass than the electrons (21), the charged particles (22) are lower in drift speed than the electrons (21). Therefore, after a single discharge step, the charged particles (22) temporarily remain between the electrodes (13) and (14) (see FIG. 4B). In this case, time during which the charged particles (22) remain between the electrodes (13) and (14) is defined as the residence time. When every remaining charged particle (22) reaches the counter electrode (14), the electric field between the electrodes (13) and (14) returns to the original state to start discharge again (see FIG. 4C). In this way, streamer discharge occurs in cycles in the order as shown in FIGS. 4A, 4B and 4C. Due to the intermittent movement of the charged particles (22) generated in this cycle, electric current flows in the pulse form during streamer discharge.

According to the second invention, the electrodes (13) and (14) are so configured that the residence time of the charged particles (22) generated by streamer discharge is controlled to 0.17 ms or less. Owing to the configuration, the cycle of streamer discharge proceeds quickly in the above-described cycle of FIGS. 4A, 4B and 4C, whereby the frequency of the sound derived from the current which flows in the pulse form during streamer discharge becomes 6 kHz or higher. Therefore, the frequency of the sound made by streamer discharge exceeds the range of 1 kHz or higher to less than 6 kHz which is easily perceivable by the human hearing. Thus, the sound made by streamer discharge is reduced.

According to a third invention, a discharge device comprises a discharge electrode (13); a counter electrode (14) which is opposed to the discharge electrode (13); and a power source (18) connected to both of the discharge electrode (13) and the counter electrode (14) to apply a discharge voltage thereto.

A feature of the discharge device is that the distance (L) between the discharge electrode (13) and the counter electrode (14) is not more than 10 mm.

In a conventional technique for causing streamer discharge, the electrodes are arranged to have a distance longer than 10 mm between them. If the distance between the electrodes is extended, the charged particles (22) have to travel a longer distance to reach the counter electrode (14), resulting in longer residence time. As a result, the frequency of the sound made by streamer discharge decreases. That is, the frequency of the sound is prone to be within the range of 1 kHz or higher to less than 6 kHz which is easily perceivable by the human hearing.

According to the third invention, the distance (L) between the discharge electrode (13) and the counter electrode (14) is not more than 10 mm, which is smaller than the conventionally employed distance, whereby the distance that the charged particles (22) generated by streamer discharge have to travel is reduced. Therefore, the residence time during which the charged particles (22) remain between the electrodes (13) and (14) is also reduced, thereby increasing the frequency of the sound. Thus, the frequency (center frequency) of the sound made by streamer discharge exceeds the range which is easily perceivable by the human hearing, thereby reducing the discharge sound.

According to a fourth invention, in the discharge device of the first, second or third invention, the discharge electrode (13) has two or more projecting discharge ends (17), the counter electrode (14) is flat, and the tips of the discharge ends (17) of the discharge electrode (13) are opposed to an electrode surface of the counter electrode (14).

The term "flat" which describes the shape of the counter electrode (14) signifies that the counter electrode (14) is small in thickness and planular. For example, the counter electrode (14) may be in the form of a flat plate, a punched plate having holes or a mesh.

According to the fourth invention, two or more projecting discharge ends (17) are provided on the discharge electrode (13) and the counter electrode (14) opposed to the discharge ends (17) is flat. With this configuration, streamer discharge occurs between the discharge ends (17) and the counter electrode (14).

As described above, streamer discharge is caused by the movement of the electrons (21) and the charged particles (22) between the discharge electrode (13) and the counter electrode (14). At this time, a leader (23) (miniscule arc) extends continuously from the discharge electrode (13) toward the counter electrode (14). In a region where the miniscule arc is generated (discharge region), active species (fast electrons, ions, radicals and other excited molecules) for decomposing a target gas are generated.

The electrode surface of the discharge end (17) is relatively smaller in area than the electrode surface of the counter electrode (14). Therefore, the miniscule arc extends in a flared shape from the discharge end (17) toward the counter electrode (14). This expands the discharge region, thereby generating the active species for decomposing the target gas in a larger area.

Since the discharge electrode (13) is provided with two or more discharge ends (17), the miniscule arc extends in a flared shape from each of the discharge ends (17) toward the counter electrode (14). Therefore, the discharge region between the discharge electrode (13) and the counter electrode (14) becomes much larger, thereby generating a larger amount of the active species.

According to a fifth invention, in the discharge device of the fourth invention, the discharge ends (17) of the discharge electrode (13) are flat.

According to the fifth invention, the discharge ends (17) are made flat and thin, whereby the discharge surfaces of the discharge ends (17) are reduced. By reducing the discharge surfaces in this manner, more non-uniform electric field is created in the discharge region.

If the distance (L) between the discharge electrode (13) and the counter electrode (14) is reduced, spark discharge is likely to occur. Therefore, if the voltage is raised too high, stable streamer discharge may possibly be hard to occur. On the other hand, according to the fifth invention, the discharge surface of the discharge electrode (13) is reduced to generate more non-uniform electric field in the discharge region. Accordingly, the distance (L) between the electrodes (13) and (14) can be reduced while the occurrence of spark discharge is prevented. As a result, time required for the charged particles (22) to reach the counter electrode (14) is reduced, thereby increasing the frequency of the sound made by streamer discharge. Thus, the discharge sound is reduced to a further extent.

Further, field intensity in the discharge region increases as a result of the reduction in discharge surface of the discharge electrode (13) and the reduction in distance (L) between the electrodes (13) and (14). Since the drift speed of the charged particles (22) is in proportion to the field intensity, an increase in field intensity causes an increase in drift speed of the charged particles (22) moving toward the counter electrode (14). As a result, the residence time of the charged particles (22) remaining between the electrodes (13) and (14) is reduced. This allows further increase in frequency of the sound made by streamer discharge, thereby reducing the noise of streamer discharge.

According to a sixth invention, in the discharge device of the first, second or third invention, the discharge electrode (13) is linear or rod-shaped and arranged substantially parallel to the counter electrode (14). The term "linear or rod-shaped" which describes the shape of the discharge electrode (13) signifies a narrow shape whose cross sectional area is substantially uniform at any position. Further, the expression "the discharge electrode (13) is arranged substantially parallel to the counter electrode (14)" signifies that the discharge electrode (13) is arranged parallel to the electrode surface of the counter electrode (14). The electrode surface of the counter electrode (14) may be flat, curved, or in the form of a narrow line or a rod.

According to the sixth invention, streamer discharge occurs from the tips of the discharge electrode (13) arranged substantially parallel to the counter electrode (14) toward the electrode surface of the counter electrode (14). Even if the tips of the discharge electrode (13) are worn by the fast electrons and active species generated during discharge, the distance between the discharge electrode (13) and the counter electrode (14) is kept unchanged because the discharge electrode (13) is arranged substantially parallel to the counter electrode (14).

The tips of the linear or rod-shaped discharge electrode (13) do not change in shape even if they are worn. Therefore, even if the discharge electrode (13) is worn, the discharge characteristic is maintained, causing streamer discharge with stability.

A seventh invention relates to an air purifier provided with a discharge device according to any one of the first to sixth inventions for treating a target gas by introducing the target gas between both the electrodes (13) and (14).

According to the seventh invention, the air purifier is provided with a discharge device having the functions according to any one of the first to sixth inventions. Therefore, the air purifier is given with reduced noise of streamer discharge and high decomposition ability.

According to the first invention, the discharge electrode (13) and the counter electrode (14) are so configured that the frequency of sound made by streamer discharge is controlled to 6 kHz or higher. Accordingly, the frequency of the discharge sound exceeds the range of 1 kHz or higher to less than 6 kHz which is easily perceivable by the human hearing, thereby reducing the discharge sound efficiently. Since the noise of streamer discharge is reduced, the discharge device (11) can be applied to a wide variety of air purifiers such as those for consumer use.

According to the second invention, the electrodes (13) and (14) are so configured that the residence time of the charged particles (22) is controlled to 0.17 ms or less during streamer discharge. Accordingly, the charged particles (22) travel quickly from the discharge electrode (13) to the counter electrode (14), thereby increasing the frequency of the sound made by streamer discharge. As a result, the frequency of the sound is raised to 6 kHz or higher to exceed the range which is easily perceivable by the human hearing, thereby reducing the noise of streamer discharge.

According to the third invention, the electrodes (13) and (14) are so configured that the distance (L) between the discharge electrode (13) and the counter electrode (14) is not more than 10 mm. Accordingly, the distance that the charged particles (22) have to travel during streamer discharge is reduced, allowing the charged particles (22) to move quickly to the counter electrode (14). Therefore, the frequency of the sound is raised to reduce the discharge sound with efficiency.

With the reduction of the distance (L) between the electrodes (13) and (14), a voltage required for streamer discharge is lowered. If a high voltage is required for discharge, it is necessary to ensure a certain distance between the discharge electrode (13) and the casing or a creepage distance from the aspect of electrical insulation. However, if the voltage required for streamer discharge is lowered, the distance required for the electrical insulation is also reduced. Therefore, the air purifier provided with the discharge device (11) is reduced in size.

According to the fourth invention, a projecting discharge end (17) serves as the discharge electrode (13) and the counter electrode (14) is flat and streamer discharge is caused between them. Accordingly, miniscule arc generated from the discharge end (17) extends in a flared shape toward the counter electrode (14). This expands the discharge region, thereby generating the active species for decomposing the target gas in a larger area. Therefore, the target gas is decomposed by streamer discharge with higher efficiency.

Since the discharge electrode (13) is provided with two or more discharge ends (17), the miniscule arc extends in a flared shape from each of the discharge ends (17) toward the counter electrode (14). Accordingly, the discharge region between the electrodes (13) and (14) is further expanded, generating a larger amount of active species. Therefore, the target gas is decomposed with much higher efficiency.

According to the fifth invention, the discharge ends (17) of the discharge electrode (13) are flat. Therefore, the discharge surface of the discharge electrode becomes small, thereby generating more non-uniform electric field in the discharge region. As a result, the distance (L) between the electrodes (13) and (14) is reduced without causing spark discharge. Further, with the reduction of the distance (L), the field intensity increases, thereby allowing further increase in drift speed of the charged particles (22). Thus, the frequency of the sound made by streamer discharge is raised to reduce the discharge sound to a further extent.

With the increase in field intensity between the electrodes (13) and (14), streamer discharge occurs with higher stability, whereby the target gas is more stably decomposed at high efficiency.

According to the sixth invention, the discharge electrode (13) which is linear or rod-shaped is arranged substantially parallel to the counter electrode (14). Therefore, even if the tips of the discharge electrode (13) are worn by the active species or fast electrons, the distance between the electrodes (13) and (14) is kept unchanged. Since the distance between the electrodes (13) and (14) is kept to the optimum, the effect of reducing the noise as described above is exerted with stability. Further, keeping the optimum distance between the electrodes (13) and (14) allows improvement in stability of streamer discharge by the discharge device (11).

Further, since the tips of the discharge electrode (13) are configured not to change in shape even if they are worn, the inherent discharge characteristic is maintained and streamer discharge is caused with higher stability. This prevents the occurrence of spark discharge and abnormal discharge derived from the change in tip shape of the discharge electrode (13).

According to the seventh invention, the air purifier is provided with the discharge device according to any one of the first to sixth inventions. Therefore, the air purifier is given with reduced discharge sound and high decomposition efficiency. Thus, the air purifier is applied to consumer use which requires low noise.

DETAILED DESCRIPTION OF THE INVENTION

Embodiment 1

Hereinafter, Embodiment 1 of the present invention will be described in detail with reference to the drawings.

Figure 1:
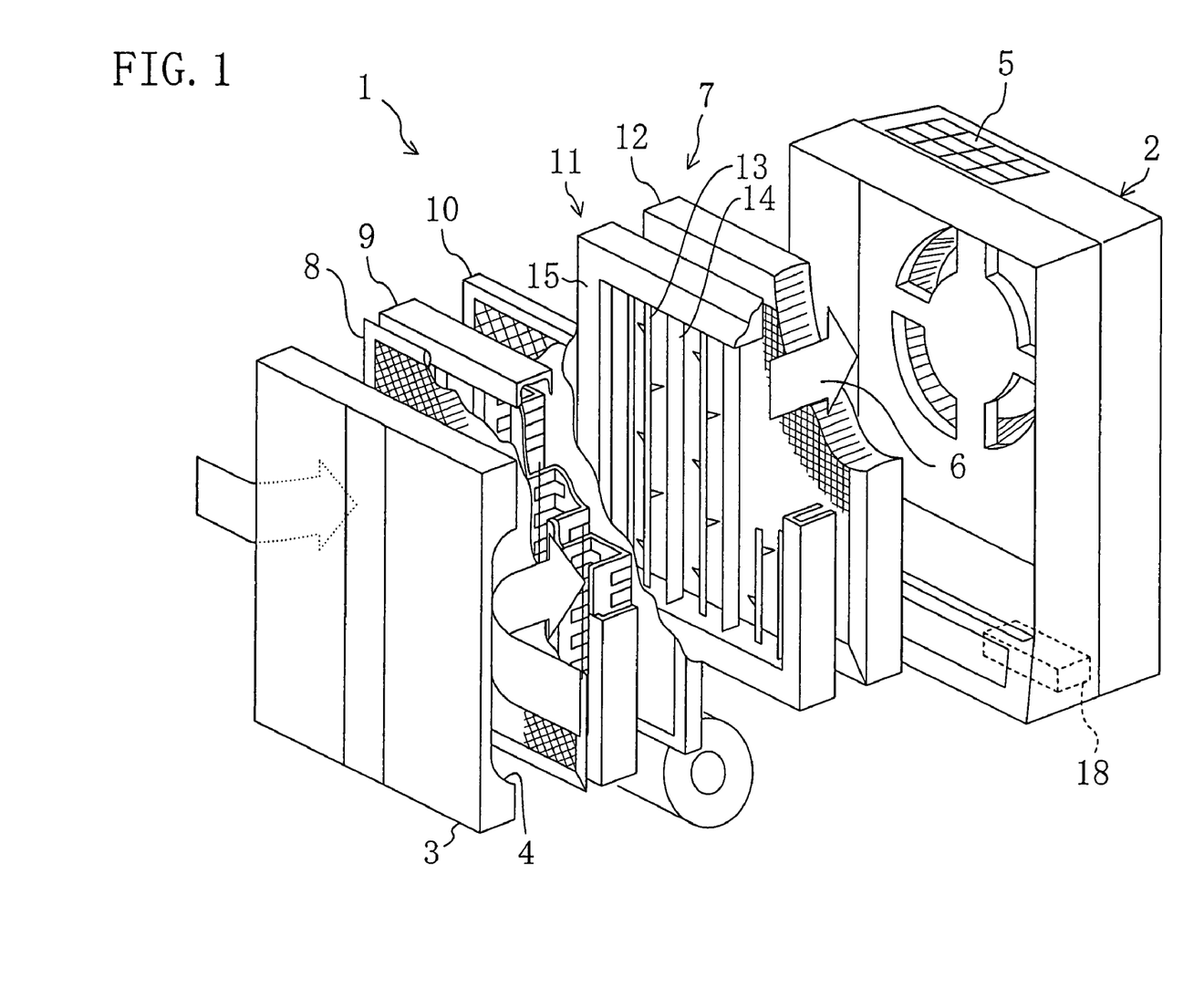
FIG. 1 is an exploded oblique view illustrating an air purifier according to Embodiment 1 of the present invention.

FIG. 1 is an exploded oblique view illustrating an air purifier (1) according to Embodiment 1 of the present invention. The air purifier (1) is a consumer air purifier for use at home or in small stores.

The air purifier (1) includes a box-shaped casing body (2) having an open side and a front cover (3) to be fitted to the open side. Air inlets (4) are formed on both sides of the front cover (3) to introduce a target gas into the air purifier. The casing body (2) is further provided with an air outlet (5) for emitting the target gas at the top side thereof, a fan (not shown) for circulating the target gas, a target gas flow path (6) and functional components (7) for air purification.

The functional components (7) include a prefilter (8), an ionization part (9), a dust collection filter (10), a discharge device (11) and a catalyst part (12).

The prefilter (8) performs pretreatment of the target gas, i.e., collects relatively large dust in the air. Then, the following ionization part (9) electrifies relatively small dust. The electrified dust is collected by the dust collection filter (10) (electrostatic filter). The discharge device (11) for causing streamer discharge and the catalyst part (12) are arranged behind the dust collection filter (10). The catalyst part (12) is of a honeycomb structure, for example, and has the catalytic function of enhancing the activity of low temperature plasma generated by discharge in the discharge device (11) to promote reaction.

Then, a detailed explanation is given of the discharge device (11).

FIG. 2A is an enlarged view of a major part illustrating an electrode configuration of the discharge device (11). FIG. 2B is a front view illustrating a major part of a discharge electrode (13).

The discharge device (11) includes discharge electrodes (13), counter electrodes (14) opposed to the discharge electrodes (13), respectively, and an electrode frame (15) which supports the electrodes (13) and (14). The discharge electrodes (13) and the counter electrodes (14) are located within the electrode frame (15) and arranged alternately at regular intervals.

As shown in FIGS. 2A and 2B, each of the discharge electrodes (13) is made of a flat discharge substrate (16) which is supported by the electrode frame (15) and two or more projecting discharge ends (17). The discharge ends (17) are flat and triangular and arranged at regular intervals on the discharge substrate (16). The flat discharge ends (17) are preferably about 0.1 mm in thickness (d). As shown in FIG. 2C, the discharge ends (17) formed on the discharge substrate (16) may be bent from the discharge substrate (16) at a certain angle in horizontal directions from the discharge substrate (16).

The counter electrodes (14) opposed to the discharge electrodes (13) are flat and attached to the electrode frame (15) such that electrode surfaces of the counter electrodes (14) are substantially orthogonal to the tips of the discharge ends (17). In this case, the distance (L) between the tip of the discharge end (17) of the discharge electrode (13) and the electrode surface of the counter electrode (14) is preferably not more than 10 mm. More preferably, the distance (L) is in the range of not less than 3 mm to not more than 10 mm. In the discharge device (11) of the present embodiment, the distance (L) is 5 mm.

Figure 2:
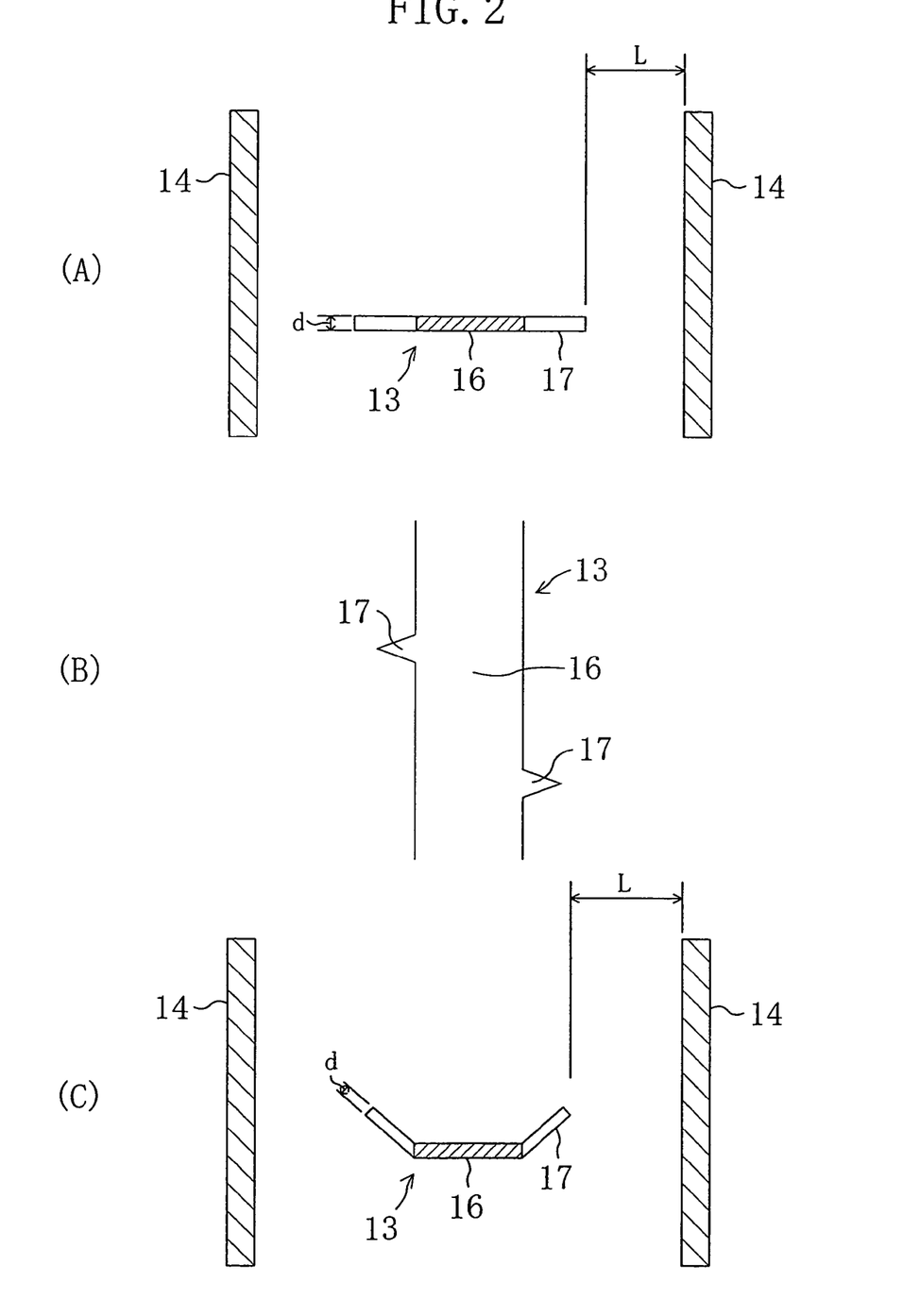
FIG. 2A is an enlarged view of a major part illustrating an electrode configuration of a discharge device.
FIG. 2B is a front view of a major part illustrating a discharge electrode and FIG. 2C is an enlarged view of a major part illustrating a variation of the electrode configuration of the discharge device.

According to the present embodiment, the discharge ends (17) are arranged on the left and right sides of the discharge substrate (16) of the discharge electrode (13) as viewed in FIG. 2. Correspondingly to this configuration, the counter electrode (14) has the electrode surfaces on both sides thereof. With this configuration, the electrodes (13) and (14) arranged alternately in the electrode frame (15) allow streamer discharge to occur at both sides of each of the discharge electrodes (13).

The discharge device (11) further includes a power source (18) for applying a discharge voltage to the discharge electrodes (13) and the counter electrodes (14). In the present embodiment, a direct voltage is employed as the discharge voltage applied by the power source (18). It is preferable to control the voltage application to keep a constant discharge current value.

Next, the operation of the air purifier (1) will be explained.

When the air purifier (1) is energized, a fan which is not shown is activated to inhale a target gas from the air inlets (4) formed in the front cover (3), thereby introducing the target gas into the flow path (6). Then, in the first step, relatively large dust in the target gas is collected and removed by the prefilter (8). In the second step, relatively small dust is electrified by the ionization part (9) and then flows downstream. The electrified dust is then collected and removed by the dust collection filter (10). In this way, most of the dust in the target gas is collected and removed by two-stage physical treatment.

Then, in the third step, the target gas which has gone through the two-stage physical treatment is introduced to the discharge device (11). As low temperature plasma which has been generated by streamer discharge between the discharge electrodes (13) and the counter electrodes (14) of the discharge device (11), the target gas passes through the low temperature plasma generating region. At this time, highly reactive active species (fast electrons, ions, radicals and other excited molecules) derived from the low temperature plasma have been generated between the electrodes (13) and (14). Upon contact with the active species, hazardous components and odorous components in the target gas are decomposed and removed. Further, since the catalyst part (12) is arranged close to the discharge device (11), the decomposition of the target gas is promoted by the catalytic function of the catalyst part (12). With this configuration, the low temperature plasma and the catalytic function exhibit a synergistic effect, thereby decomposing and removing the hazardous components and odorous components in the target gas with high efficiency.

The target gas purified by the above-described process is emitted outside in the upward direction from the air outlet (5) provided in the casing body (2).

The effect of reducing the sound made by streamer discharge was examined by experiment. The results are explained below.

Figure 3:
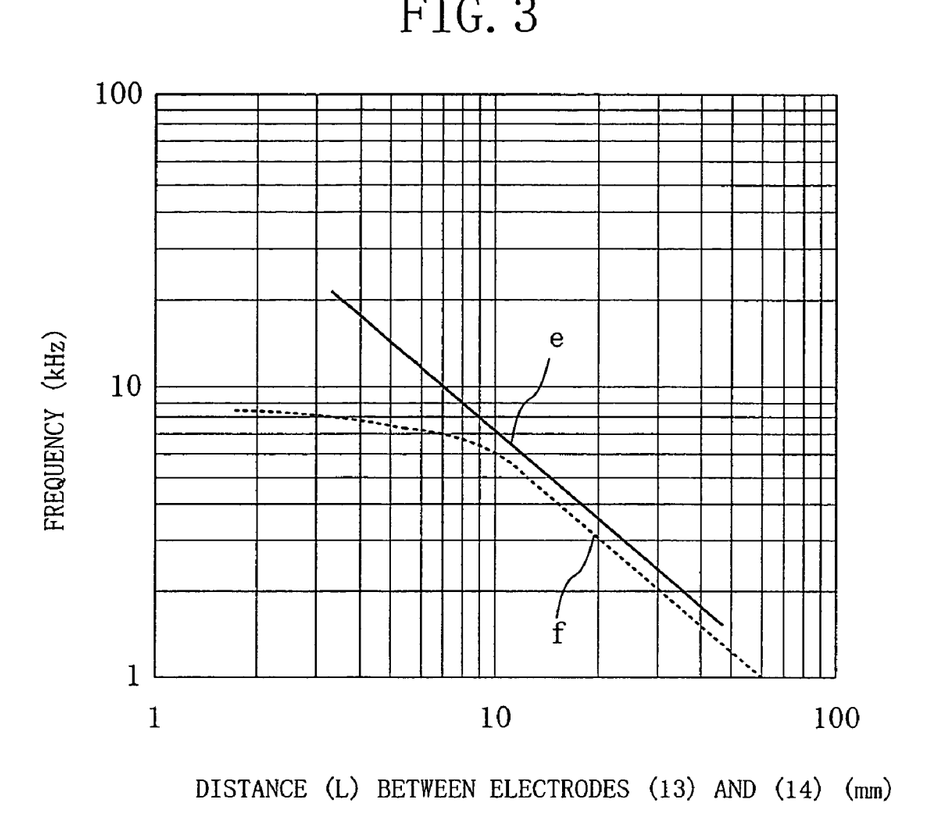
FIG. 3 is a graph illustrating a relationship between the distance from a discharge electrode to a counter electrode and the frequency of sound during streamer discharge.

FIG. 3 is a graph illustrating an experimentally-obtained relationship between the distance (L) from the discharge electrode (13) to the counter electrode (14) and the frequency of sound during streamer discharge. In this experiment, streamer discharge was caused in the discharge device (11) including the discharge electrodes (13) provided with the projecting discharge ends (17) and the flat counter electrodes (14). The frequency of the sound made by streamer discharge was measured precisely while the distance (L) between the electrodes (13) and (14) was varied. The frequency of the sound shown in FIG. 3 is a measurement of the center frequency of the sound made by streamer discharge. The center frequency mentioned herein is the frequency at which the highest sound pressure level of the discharge sound is obtained in the measurement on a frequency-by-frequency basis.

Referring to FIG. 3, a solid line (e) represents a relationship between the distance (L) and the frequency of the sound obtained when a current value (current density) per discharge electrode (13) was set to 20 µA. Further, a broken line (f) represents a relationship between the distance (L) and the frequency of the sound obtained when current was passed at a minimum current density required for streamer discharge in response to the distance (L) between the electrodes (13) and (14). That is, desired streamer discharge may occur in a region above the broken line (f), while streamer discharge does not occur in a region below the broken line (f).

As shown in FIG. 3, when the distance (L) between the discharge electrode (13) and the counter electrode (14) is reduced, the frequency of the sound made by streamer discharge increases. This is derived from the fact that the reduction of the distance (L) between the electrodes (13) and (14) allows reduction in time required for charged particles (22) generated by streamer discharge to reach the counter electrode (14), thereby reducing the residence time of the charged particles (22).

Referring to FIG. 3, when the distance (L) between the electrodes (13) and (14) during streamer discharge is 10 mm, the frequency of the sound exceeds 6 kHz on both of the lines (e) and (f). The broken line (f) indicates that, when the distance (L) is 9 mm, streamer discharge may occur at a current density of about 10 µA or higher and the frequency of the sound at that time is raised up to about 6.5 kHz. Further, when the distance (L) is 5 mm, which is the same value as that employed in this embodiment, streamer discharge may occur at a current density of about 3 µA or higher and the frequency of the sound at that time is further raised up to about 8 kHz. In this way, if the frequency of the sound is 6 kHz or higher, the discharge sound is hardly perceived by human hearing. The upper limit of the frequency of the sound is substantially 20 kHz, preferably 30 kHz, which are almost impossible for the human hearing to sense.

According to Embodiment 1 described above, the frequency of the sound made by streamer discharge becomes 6 kHz or higher when the distance (L) between the electrodes (13) and (14) during streamer discharge is not more than 10 mm. On the other hand, the residence time of the charged particles (22) between the electrodes (13) and (14) is a reciprocal of the frequency of the sound. That is, when the frequency is 6 kHz or higher, the residence time is 0.17 ms or less.

Thus, according to the present embodiment, the electrodes (13) and (14) are so configured that the frequency of the sound made by streamer discharge is controlled to 6 kHz or higher. Therefore, the frequency of the discharge sound exceeds the frequency range which is easily perceivable by the human hearing. As a result, the noise of streamer discharge is effectively reduced.

In the present embodiment, each of the discharge electrodes (13) is provided with two or more projecting discharge ends (17) and streamer discharge is carried out between the discharge end (17) and the flat counter electrode (14). This configuration expands the discharge region to generate the active species in a larger area, thereby decomposing the target gas with higher efficiency.

Since the discharge end (17) is flat and has a thickness (d) as thin as 0.1 mm, more non-uniform electric field is generated in the discharge region from the discharge end (17). Accordingly, spark discharge is less likely to occur. This allows further reduction of the distance (L) between the electrodes (13) and (14). Since the reduction of the distance (L) increases the electric field intensity, the charged particles (22) increase in drift speed, thereby reducing the residence time of the charged particles (22). Thus, the frequency of the discharge sound is further raised, thereby reducing the noise of streamer discharge to a greater extent.

In Embodiment 1 described above, a direct voltage is applied as a discharge voltage from the power source (18) of the discharge device (11). By so doing, the operation cost of the discharge device (11) is reduced. If the discharge current value of the discharge voltage is controlled to a certain level, the frequency of the streamer discharge sound is stabilized and the occurrence of spark discharge due to abnormal discharge is easily avoided. Thus, the reduction of the discharge sound is achieved.

Embodiment 2

Hereinafter, Embodiment 2 of the present invention will be described in detail with reference to the drawings.

Figure 5:
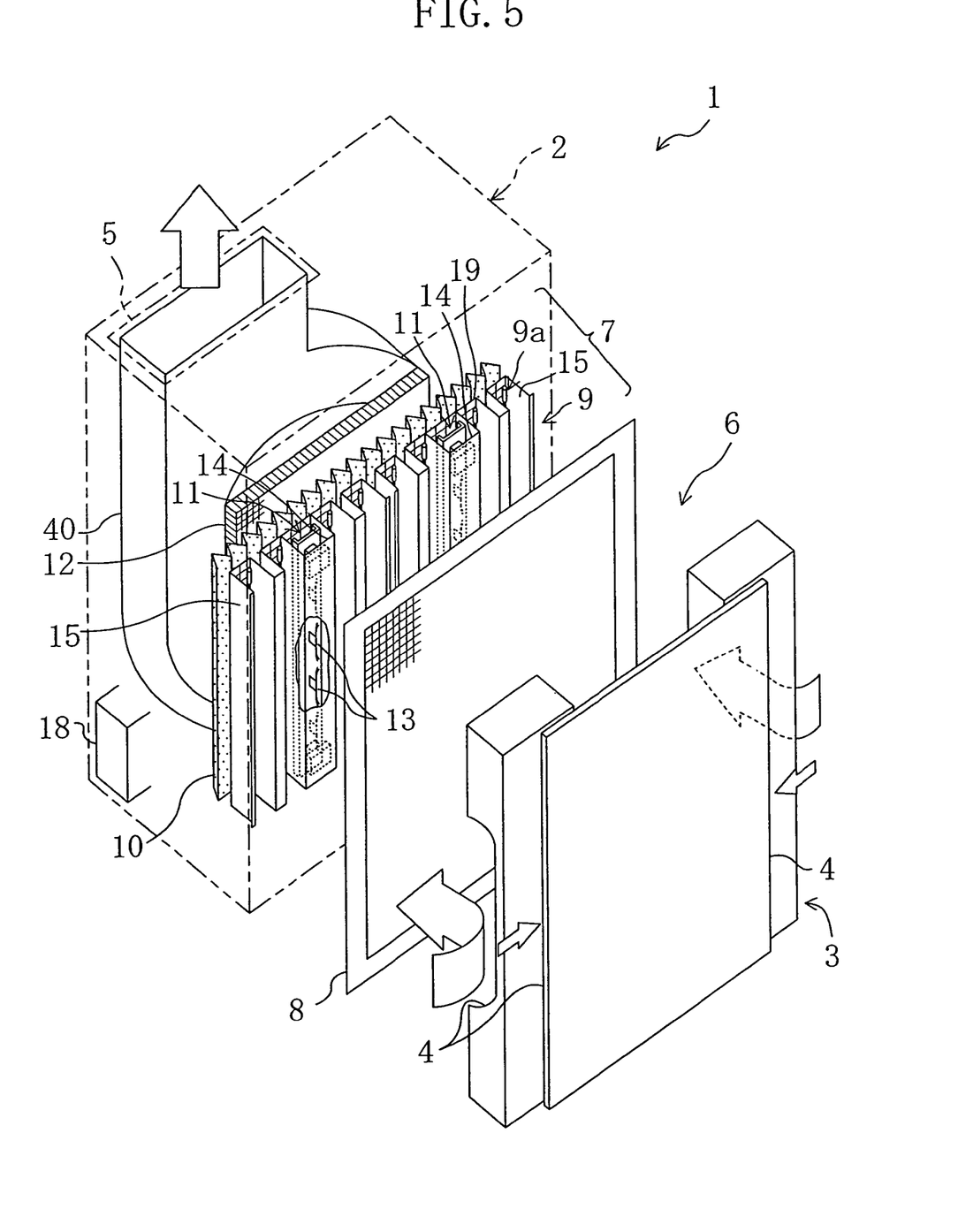
FIG. 5 is an exploded oblique view illustrating an air purifier according to Embodiment 2 of the present invention.
Figure 6:
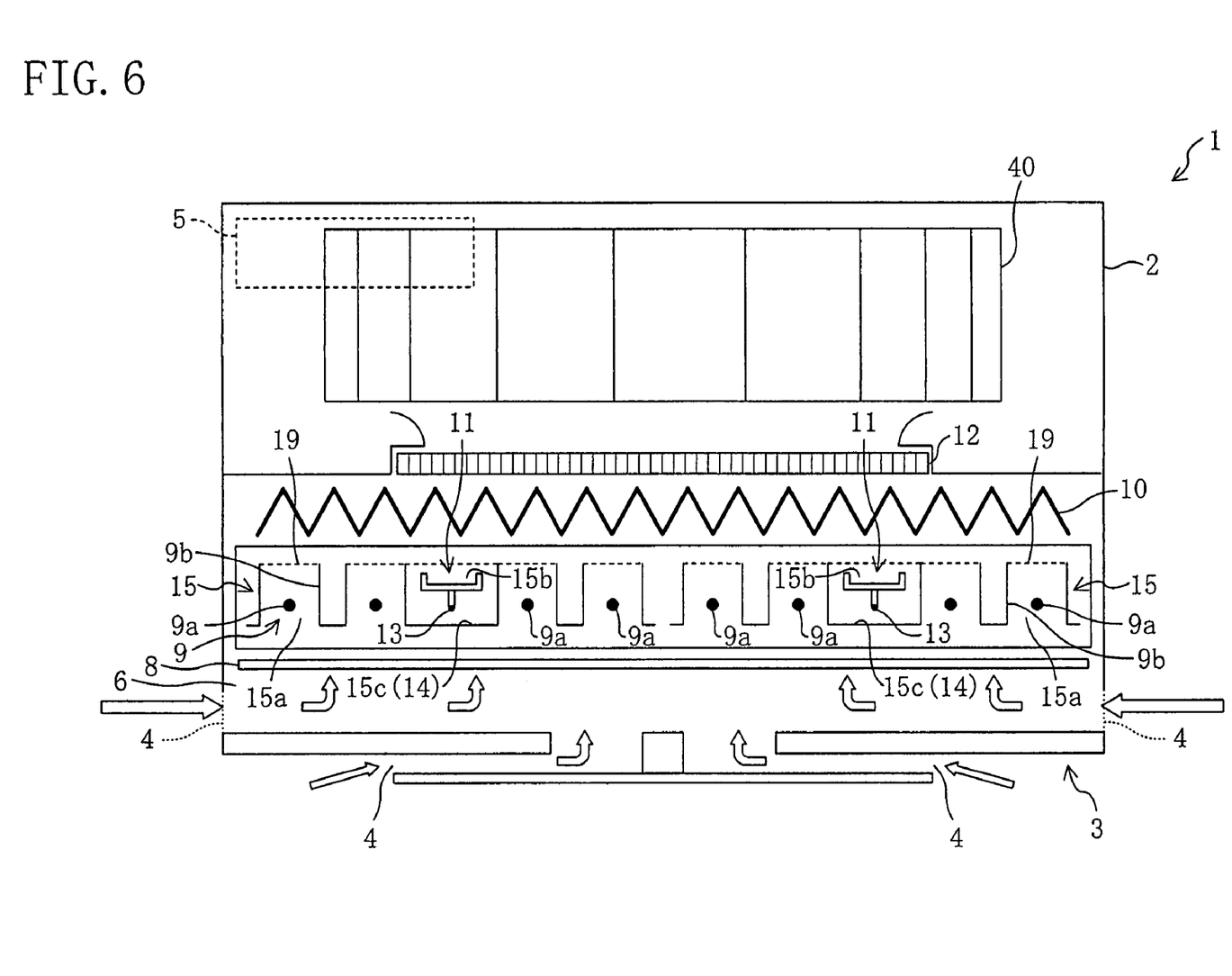
FIG. 6 is a cutaway top view illustrating the inside of the air purifier according to Embodiment 2 of the present invention.

FIG. 5 is an exploded oblique view illustrating an air purifier (1) according to Embodiment 2 of the present invention. FIG. 6 is a cutaway top view illustrating the inside of the air purifier (1). Similar to the air purifier of Embodiment 1, the air purifier (1) is a consumer air purifier for use at home or in small stores.

The air purifier (1) includes a box-shaped casing body (2) having an open side and a front cover (3) to be fitted to the open side. Air inlets (4) are formed on both sides and a front center part of the front cover (3) to introduce room air as a target gas into the air purifier. In a part of the top plate of the casing body (2) closer to the back side thereof, an air outlet (5) is formed to allow the room air to flow outside.

In the casing body (2), a flow path (6) for passing room air through it is provided between the air inlets (4) and the air outlet (5). In the flow path (6), various functional components (7) for air purification and a centrifugal blower (40) for circulating the room air in the flow path (6) are arranged in this order from the upstream of the room air flow (from the bottom in FIG. 6).

The functional components (7) include a prefilter (8), an ionization part (9), a discharge device (11), a dust collection filter (10) and a catalyst filter (12) arranged in this order from the closest to the front cover (3). Further, a power source (18) for the discharge device (11) is provided in a lower back part of the casing body (2) of the air purifier (1).

The prefilter (8) collects relatively large dust in the room air. The ionization part (9) electrifies relatively small dust which has passed through the prefilter (8). The electrified dust is collected by the dust collection filter (electrostatic filter) (10) placed at the downstream of the ionization part (9). The ionization part (9) is made of two or more ionization wires (9a) and counter electrodes (9b) corresponding to the ionization wires (9a).

The ionization wires (9a) are arranged in front of a corrugated member (15) which is in a corrugated configuration or in connected substantially U shapes when viewed in horizontal section. In the present embodiment, two corrugated members (15) are arranged from side to side. Each of the corrugated members (15) is formed with a plurality of front open areas (15a) and the ionization wires (9a) are arranged in the front open areas (15a), respectively, so as to extend from the upper end to the lower end of the corrugated member (15). The counter electrodes (9b) corresponding to the ionization wires (9a) are formed by parts of the corrugated members (15) which serves as the walls defining the front open areas (15a). Mesh plates (19) are attached to rearward surfaces the corrugated members (15) so that they are parallel to the dust collector filter (10).

The discharge device (11) includes two or more discharge electrodes (13) and flat counter electrodes (14) opposed to the discharge electrodes (13), respectively.

The discharge electrodes (13) are linear or rod-shaped and arranged behind the corrugated members (15). As shown in an enlarged oblique view of the discharge device (11) of FIG. 7A, the discharge electrodes (13) are supported by electrode holders (20) extending in the vertical direction in rear open areas (15b) of the corrugated members (15). Each of the electrode holders (20) is substantially U-shaped when viewed in horizontal section and provided at desired positions with forwardly bent support plates (20a), respectively. The linear or rod-shaped discharge electrode (13) is supported by the edge portion of the support plate (20a) which is crimped to hold the discharge electrode (13) (see a horizontal section of the discharge device in FIG. 7B). In this way, the upper and lower ends of the discharge electrode (13) protrude from the support plate (20a) in the vertical direction. In the present embodiment, the discharge electrodes (13) are made of tungsten and have a diameter of about 0.2 mm.

Figure 7:
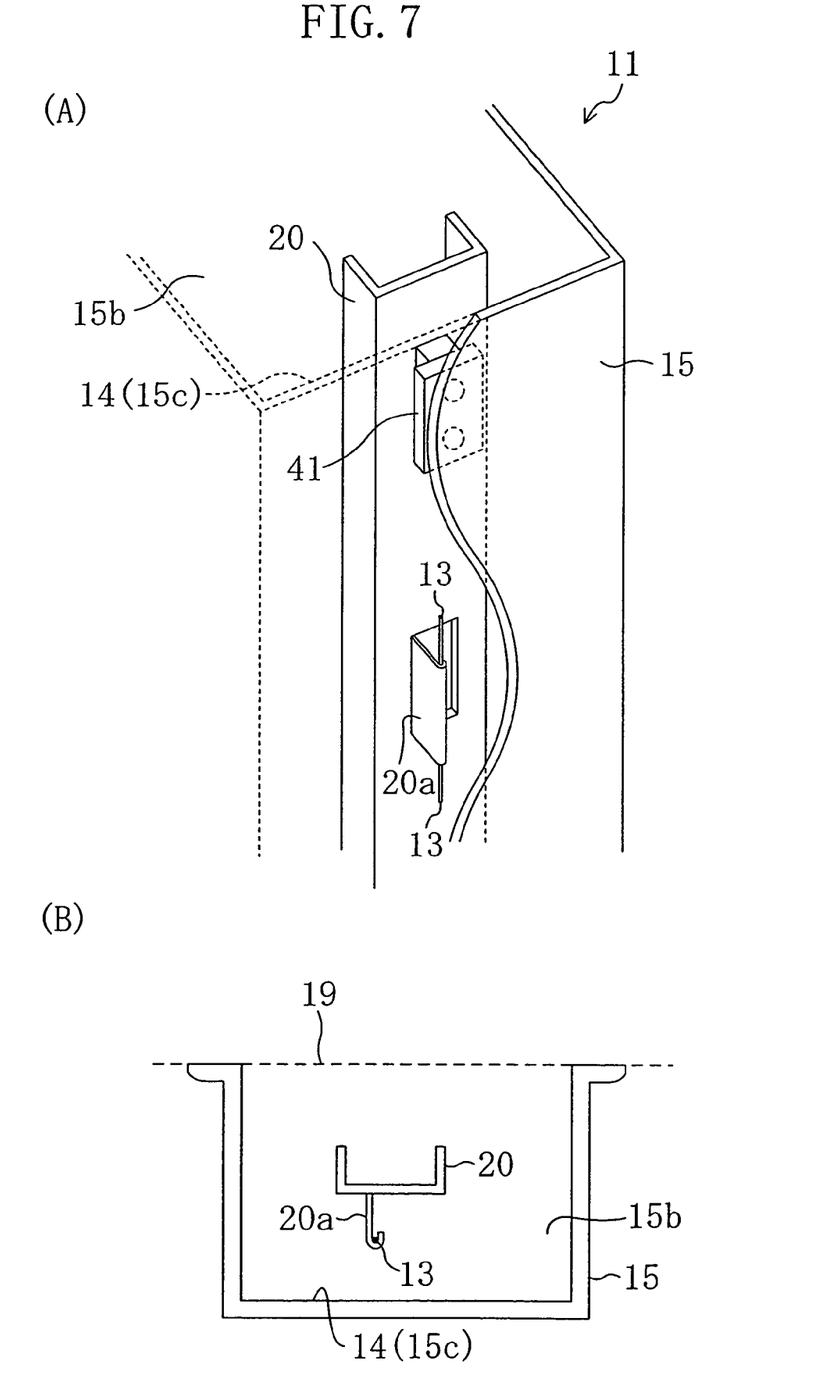
FIG. 7A is an enlarged view of a major part illustrating an electrode configuration of a discharge device and FIG. 7B is a horizontal section of the discharge device.

The counter electrodes (14) are formed by parts of the corrugated members (15) which have first surfaces (rear surfaces) (15c) defining the rear open areas (15b) in which the discharge electrodes (13) are thus arranged. The first surfaces (15c) function as electrode surfaces opposing to the discharge electrodes (13). Thus, the discharge electrodes (13) protruding from the support plates (13a) are arranged substantially parallel to the electrode surfaces of the counter electrodes (14). Further, spacers (41) are arranged at the upper and lower ends of each of the counter electrodes (14) to fit between the counter electrode (14) and the electrode holder (20). In this embodiment, the spacers (41) are made of insulation porcelain. The spacers (41) keep a certain distance (L) between the tips of the discharge electrode (13) and the counter electrode (14). In this embodiment, the distance (L) between the electrodes (13) and (14) is set to 6.1±0.3 mm.

The electrostatic filter (10) is positioned at the downstream of the discharge device (11). The electrostatic filter (10) collects relatively small dust electrified by the ionization part (9) on the upstream surface and supports a photocatalyst (photosemiconductor) on the downstream surface. The photocatalyst is further activated by highly reactive substances (active species such as electrons, ions, ozone and radicals) in low temperature plasma generated by discharge in the discharge device (11) to promote decomposition of the hazardous components and odorous components in room air. The photocatalyst is, for example, titanium dixoxide, zinc oxide, tungsten oxide or cadmium sulfide. The electrostatic filter (10) is a so-called pleated filter which is corrugated when viewed in horizontal section.

The catalyst filter (12) is arranged at the downstream of the electrostatic filter (10). The catalyst filter (12) is made of a base material of a honeycomb structure and a plasma catalyst supported on the surface of the base material. Like the above-described photocatalyst, the plasma catalyst is further activated by the highly reactive substances (active species such as electrons, ions, ozone and radicals) in the low temperature plasma generated by discharge in the discharge device (11) to promote decomposition of the hazardous components and odorous components in room air. The plasma catalyst may be a manganese-based catalyst, a noble metal-based catalyst or a catalyst of these kinds added with an adsorbent such as activated carbon.

During the operation of the air purifier (1), the centrifugal blower (40) is working and room air as a target gas is passed through the flow path (6) in the casing body (2). In this state, a high voltage is applied from the power source (18) to the ionization part (9) and the discharge device (11).

When room air is introduced into the casing body (2), relatively large dust in the air is collected by the prefilter (8). The room air passed through the prefilter (8) flows toward the ionization part (9). Due to discharge caused between the ionization wires (9a) and the counter electrodes (9b) in the ionization part (9), relatively small dust in the room air is electrified. The room air containing the electrified dust flows toward the electrostatic filter (10) and the electrified dust is collected by the electrostatic filter (10).

In the discharge device (11), low temperature plasma has been generated by streamer discharge between the discharge electrodes (13) and the counter electrodes (14). The low temperature plasma generated by the discharge device (11) flows downstream together with the room air.

The low temperature plasma contains highly reactive substances (active species). Upon contact with the room air, the highly reactive substances decompose hazardous components and odorous components contained in the room air. When the active species reach the electrostatic filter (10), they are further activated by the photocatalyst supported on the electrostatic filter (10) to enhance the decomposition of the hazardous and odorous components in the room air. Further, when the active species reach the catalyst filter (12), they are much more activated to decompose the hazardous and odorous components to a greater extent.

In this manner, the room air is purified by removing the dust, hazardous components and odorous components, and then emitted outside by the centrifugal blower (40) from the air outlet (5).

In Embodiment 2 described above, the distance (L) between the discharge electrode (13) and the counter electrode (14) in the discharge device (11) is set to 6.1±0.3 mm, i.e., not more than 10 mm. As a result, the frequency of the discharge sound made by streamer discharge is controlled to 6 kHz or higher. That is, the frequency of the discharge sound made by streamer discharge exceeds the frequency range which is easily perceivable by the human hearing. Therefore, also in Embodiment 2, the noise of streamer discharge is reduced.

In Embodiment 2, the rod-shaped discharge electrode (13) and the counter electrode (14) are arranged parallel to each other. Therefore, even if the tips of the discharge electrode (13) are worn by the active species and fast electrons, the distance between the electrodes (13) and (14) is kept unchanged. Since the distance (L) between the electrodes (13) and (14) is kept to the optimum, the above-described effect of reducing the noise is surely exerted. Further, keeping the optimum distance between the electrodes (13) and (14) allows improvement in stability of streamer discharge.

Further, in Embodiment 2, the tips of the discharge electrode (13) do not change in shape even if they are worn. Therefore, the inherent discharge characteristic is maintained and streamer discharge is caused with higher stability. This prevents the occurrence of spark discharge and abnormal discharge derived from the change in tip shape of the discharge electrode (13).

Other Embodiments

In addition to Embodiments described above, the present invention may be configured as follows.

In Embodiment 1, the discharge ends (17) arranged on the discharge electrode (13) are flat and triangular. However, for example, the discharge ends (17) may be prism-shaped or tapered down toward the distal end thereof.

In Embodiment 1, the discharge ends (17) are arranged on both sides of the discharge substrate (16) to constitute the discharge electrode (13) and the counter electrodes (14) are arranged on both sides of the discharge electrode (13) to cause streamer discharge. However, the discharge ends (17) are not necessarily provided on both sides of the discharge substrate (16). They may be arranged on one side of the discharge substrate (16). In this case, the counter electrode (14) is attached to the electrode frame (15) such that the counter electrode (14) is opposed to the discharge ends (17) arranged on one side of the discharge substrate (16).

In Embodiments described above, a direct voltage is applied as the discharge voltage from the power source (18). However, the discharge voltage may be an alternating voltage or a pulse voltage.

In Embodiments described above, the catalyst filter (12), which is made of a base material and a plasma catalyst supported thereon such as a manganese-based catalyst or a noble metal-based catalyst, is arranged at the downstream of the discharge device (11). However, for example, the catalyst filter (12) at the downstream of the discharge device (11) may be replaced with an adsorption part made of a base material and an adsorbent supported thereon such as activated carbon or zeolite.

As described above, the present invention is useful for a discharge device which performs streamer discharge and an air purifier.

What is claimed is:

1. A discharge device comprising:

a discharge electrode;

a counter electrode opposed to the discharge electrode; and a power source connected to both of the discharge electrode and the counter electrode to apply a discharge voltage thereto, the discharge electrode being linear or rod-shaped, and the discharge device being configured so that streamer discharge occurs from a tip of the discharge electrode to an electrode surface of the counter electrode;

the discharge electrode having a same cross section orthogonal to an axis of the discharge electrode from the tip to a base end of the discharge electrode;

the electrode surface of the counter electrode being a flat surface parallel to the discharge electrode, and the discharge electrode and the counter electrode being spaced apart by a distance not more than 10 mm.

2. An air purifier provided with the discharge device according to claim 1, wherein the discharge device is configured and arranged to receive a target gas between both the electrodes to treat the target gas.

3. The discharge device according to claim 1, wherein the power source is configured to apply a discharge voltage to both of the discharge electrode and the counter electrode so that the discharge electrodes has an electrical potential greater than that of the counter electrode.

4. An air purifier provided with the discharge device according to claim 3, wherein the discharge device is configured and arranged to receive a target gas between both the electrodes to treat the target gas.

\* \* \* \* \*